US007531332B2

(12) United States Patent
Livshits et al.

(10) Patent No.: US 7,531,332 B2
(45) Date of Patent: May 12, 2009

(54) **METHOD FOR PRODUCING A LOWER ALKYL ESTER OF α-L-ASPARTYL-L-PHENYLALANINE USING *ESCHERICHIA* BACTERIA**

(75) Inventors: Vitaliy Arkadyevich Livshits, Moscow (RU); Maria Viacheslavovna Vitushkina, Moscow (RU); Mikhail Markovich Gusyatiner, Moscow (RU); Mikhail Kharisovich Ziyatdinov, Moscow (RU); Valery Zavenovich Akhverdian, Moscow (RU); Ekaterina Alekseevna Savrasova, Moscow (RU); Vera Georgievna Doroshenko, Moscow (RU); Sergey Vladimirovich Mashko, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 21 days.

(21) Appl. No.: 11/761,465

(22) Filed: Jun. 12, 2007

(65) Prior Publication Data

US 2008/0153138 A1    Jun. 26, 2008

Related U.S. Application Data

(62) Division of application No. 10/302,983, filed on Nov. 25, 2002, now Pat. No. 7,259,003.

(30) Foreign Application Priority Data

Nov. 23, 2001    (RU) ............................. 2001131570

(51) Int. Cl.
*C12P 7/62* (2006.01)
*C07K 14/00* (2006.01)
*C07H 21/00* (2006.01)
*C12P 13/04* (2006.01)
*C12P 21/00* (2006.01)
*C12N 15/00* (2006.01)
*C12N 1/21* (2006.01)

(52) U.S. Cl. .................... 435/135; 435/106; 435/320.1; 435/69.1; 435/252.33; 530/350; 536/23.1

(58) Field of Classification Search ............. 435/320.1, 435/69.1, 252.33, 106, 135; 530/350; 536/23.1
See application file for complete search history.

(56) References Cited

U.S. PATENT DOCUMENTS

| 3,786,039 | A | 1/1974 | Ariyoshi et al. |
| 5,175,107 | A | 12/1992 | Debabov et al. |
| 5,534,421 | A | 7/1996 | Livshits et al. |
| 5,538,873 | A | 7/1996 | Debabov et al. |
| 5,631,157 | A | 5/1997 | Debabov et al. |
| 5,658,766 | A | 8/1997 | Livshits et al. |
| 5,705,371 | A | 1/1998 | Debabov et al. |
| 5,972,663 | A | 10/1999 | Winterhalter et al. |
| 5,976,843 | A | 11/1999 | Debabov et al. |
| 6,132,999 | A | 10/2000 | Debabov et al. |
| 6,165,756 | A | 12/2000 | Debabov et al. |
| 6,297,031 | B1 | 10/2001 | Debabov et al. |
| 6,303,348 | B1 | 10/2001 | Livshits et al. |
| 6,653,111 | B2 | 11/2003 | Debabov et al. |
| 6,737,255 | B2 | 5/2004 | Livshits et al. |
| 6,887,691 | B2 | 5/2005 | Livshits et al. |
| 6,960,455 | B2 | 11/2005 | Livshits et al. |
| 6,979,560 | B1 | 12/2005 | Livshits et al. |
| 7,138,266 | B2 | 11/2006 | Debabov et al. |
| 7,179,623 | B2 | 2/2007 | Livshits et al. |
| 7,186,531 | B2 | 3/2007 | Akhverdian et al. |
| 2002/0058314 | A1 | 5/2002 | Livshits et al. |
| 2003/0148473 | A1 | 8/2003 | Livshits et al. |
| 2003/0157667 | A1 | 8/2003 | Vitushkina et al. |
| 2004/0132165 | A1 | 7/2004 | Akhverdian et al. |
| 2005/0112731 | A1 | 5/2005 | Kashiwagi et al. |
| 2005/0181488 | A1 | 8/2005 | Akhverdian et al. |
| 2005/0191684 | A1 | 9/2005 | Zimenkov et al. |
| 2005/0202543 | A1 | 9/2005 | Livshits et al. |
| 2005/0214911 | A1 | 9/2005 | Marchenko et al. |
| 2005/0239175 | A1 | 10/2005 | Tabolina et al. |
| 2005/0239177 | A1 | 10/2005 | Livshits et al. |
| 2006/0014257 | A1 | 1/2006 | Katashkina et al. |

(Continued)

FOREIGN PATENT DOCUMENTS

EP    0 877 090    11/1998

(Continued)

OTHER PUBLICATIONS

U.S. Appl. No. 09/466,935, Livshits et al., filed Dec. 20, 1999.

(Continued)

*Primary Examiner*—Delia M Ramirez
(74) *Attorney, Agent, or Firm*—Shelly Guest Cermak; Cermak Kenealy Vaidya & Nakajima LLP

(57) ABSTRACT

A method for producing an L-amino acid, such as L-phenylalanine and L-threonine, is provided using an *Escherichia* bacterium, wherein the L-amino acid productivity of said bacterium is enhanced by enhancing the activity of the protein encoded by the yedA gene. A further method is provided for producing a lower alkyl ester of α-L-aspartyl-L-phenylalanine by producing L-phenylalanine by cultivating an *Escherichia coli* bacterium in a medium, wherein said bacterium has the ability to produce L-phenylalanine, and synthesizing the lower alkyl ester of α-L-aspartyl-L-phenylalanine from aspartic acid, or a derivative thereof, and the produced L-phenylalanine.

5 Claims, No Drawings

U.S. PATENT DOCUMENTS

| | | |
|---|---|---|
| 2006/0035348 A1 | 2/2006 | Gulevich et al. |
| 2006/0063240 A1 | 3/2006 | Katashkina et al. |
| 2006/0088919 A1 | 4/2006 | Rybak et al. |

FOREIGN PATENT DOCUMENTS

| | | |
|---|---|---|
| EP | 0 994 190 | 4/2000 |
| EP | 1 013 765 | 6/2000 |
| EP | 1 016 710 | 7/2000 |
| RU | 974817 | 8/1990 |
| WO | WO97/23597 | 7/1997 |
| WO | WO01/70955 | 9/2001 |

OTHER PUBLICATIONS

U.S. Appl. No. 60/586,222, Akhverdian et al., filed Jul. 9, 2004.
U.S. Appl. No. 60/601,144, Akhverdian et al., filed Aug. 13, 2004.
U.S. Appl. No. 60/604,698, Zimenkov et al., filed Aug. 27, 2004.
U.S. Appl. No. 60/703,444, Rybak et al., filed Jul 29, 2005.
U.S. Appl. No. 60/714,844, Filippov et al., filed Sep. 8, 2005.
U.S. Appl. No. 60/714,848, Filippov et al., filed Sep. 8, 2005.
U.S. Appl. No. 60/714,849, Filippov et al., filed Sep. 8, 2005.
U.S. Appl. No. 60/723,923, Filippov et al., filed Oct. 6, 2005.
U.S. Appl. No. 60/723,924, Filippov et al., filed Oct. 6, 2005.
U.S. Appl. No. 60/723,929, Filippov et al., filed Oct. 6, 2005.
U.S. Appl. No. 11/276,522, Livshits et al., filed Mar. 3, 2006.
U.S. Appl. No. 60/807,842, Filippov et al., filed Jul. 20, 2006.
U.S. Appl. No. 60/807,843, Filippov et al., filed Jul. 20, 2006.
U.S. Appl. No. 60/807,845, Filippov et al., filed Jul. 20, 2006.
U.S. Appl. No. 11/536,863, Zakataeva et al., filed Sep. 29, 2006.
U.S. Appl. No. 60/829,697, Rybak et al., filed Oct. 17, 2006.
U.S. Appl. No. 60/829,706, Filippov et al., filed Oct. 17, 2006.
U.S. Appl. No. 60/829,923, Filippov et al., filed Oct. 18, 2006.
U.S. Appl. No. 60/829,926, Rybak et al., filed Oct. 18, 2006.
U.S. Appl. No. 60/736,830, Filippov et al., filed Nov. 19, 2006.
Abstracts of 17th International Congress of Biochemistry and Molecular Biology in conjunction with 1997 Annual Meeting of the American Society for Biochemistry and Molecular Biology, Abstract No. 457, Aug. 24-29, 1997.
Aleshin, V. V., et al., "A new family of amino-acid-efflux proteins," TIBS Trends in Biochem. Sci. 1999;24(4):133-135.
Astaurova, O. B., et al., "Animation in Strains of *Escherichia coli* Which Effectively Synthesize Threonine," Appl. Biochem. Microbiol. 1985;21(5):485-490.
Astaurova, O. B., et al., "Comparative Study of Amino-Acid-Producing E. Coli Strains," Appl. Biochem. Microbiol. 1991;27(5):556-561.
Bhagwat, A. S., et al., "Cloning and Characterization of the *dcm* Locus of *Escherichia coli* K-12," J. Bacteriol. 1986;166(3):751-755.
Blattner, F. R., et al., "The Complete Genome Sequence of *Escherichia coli* K-12," Abstract p. 1-9 of Science, vol. 277, No. 5331, GenBank, AN AE000287, pp. 1453-1474, 1997.
Blattner, F.R., et al., "The Complete Genome Sequence of *Escherichia coli* K-12," Abstract p. 1-3 of Science, vol. 277, No. 5331, GenBank, AN NC_000913, pp. 1453-1474, 1997.
Blattner, F.R., et al., "The Complete Genome Sequence of *Escherichia coli* K-12," Abstract pp. 1-2 of Science, vol. 277, No. 5331, GenBank, AN NP_416468, pp. 1453-1474, 1997.
Blattner, F. R., et al., "The Complete Genome Sequence of *Escherichia coli* K-12," Science 1997;277(5331):1453-1474.
Branden, C., et al., Introduction to Protein Structure, Garland Publishing, Inc., New York, pp. 247, 1991.
Carlton, G. J., et al., "The Production of L-Phenylalanine by Polyazetidine Immobilized Microbes," Biotechnol. 1986;4:317-320.
Chistoserdov, A. Y., et al., "Broad Host Range Vectors Derived from an RSF1010::Tn1 Plasmid," Plasmid 1986;16:161-167.
International Search Report for PCT Patent App. No. PCT/JP02/12202 (Mar. 4, 2003).
Search Report for EP Patent App. No. 02788635.7 (Dec. 10, 2004).
Dassler, T., et al., "Identification of a Major Facilitator Protein from *Escherichia coli* Involved in Efflux of Metabolites of the Cysteine Pathway," Mol. Microbiol. 2000;36(5):1101-1112.
Gusyatiner, M. M., et al., "Investigation of the relA Gene Function in the Expression of Amino Acid Operons," Genetika (Genetics) 1978;XIV(6):957-968.
Gold, L., et al., "Translational Initiation in Prokaryotes," Ann. Rev. Microbiol. 1981;35:365-403.
Hui, A., et al., "Mutagenesis of the Three Bases Preceding the Start Codon of the β-Galactosidase mRNA and Its Effect on Translation in *Escherichia coli*," The EMBO J 1984;3(3):623-629.
Itoh, T., et al., "A 460-kb DNA Sequence of the *Escherichia coli* K-12 Genome Corresponding to the 40.1-50.0 min Region on the Linkage Map," DNA Res. 1996;3:379-392.
Lehninger, et al., Principles of Biochemistry, 1997, Worth Publishers, Second Edition, pp. 697-715.
Meinkoth and Wahl, Current Protocols in Molecular Biology, Hybridization Analysis of DNA Blots, pp. 2.10.8-2.10-11, 1993.
Seffernick, J. L., et al., "Melamine Deaminase and Atrazine Chlorohydrolase: 98 Percent Identical but Functionally Different," J. Bacteriol. 2001;183(8):2405-2410.
Witkowski, A., et al., "Conversion of a β-Ketoacyl Synthase to a Malonyl Decarboxylase by Replacement of the active-Site Cysteine with Glutamine," Biochem. 1999;38:11643-11650.
Zakataeva, N. P., et al., "Characterization of a Pleiotropic Mutation that Confers Upon *Escherichia coli* Cells Resistance to High Concentrations of Homoserine and Threonine," FASEB J. 1997;11(9):A935.
Zakataeva, N. P., et al., "The novel transmembrane *Escherichia coli* proteins involved in the amino acid efflux," FEBS Letters 1999;452:228-232.

METHOD FOR PRODUCING A LOWER ALKYL ESTER OF α-L-ASPARTYL-L-PHENYLALANINE USING *ESCHERICHIA* BACTERIA

This application is a divisional under 35 U.S.C. §120 of U.S. patent application Ser. No. 10/302,983, filed Nov. 25, 2002, which issued as U.S. Pat. No. 7,259,003 on Aug. 21, 2007 and this application also claims priority under 35 U.S.C. §119 to RU 2001131570, filed Nov. 23, 2001.

BACKGROUND OF THE INVENTION

1. Field of the Invention

The present invention is related to biotechnology, specifically to a method for producing L-amino acids by fermentation, and more specifically to a gene obtained from *Escherichia coli*. This gene is useful for improving L-amino acid productivity of the bacterium, for example, L-phenylalanine and L-threonine.

2. Brief Description of the Related Art

Conventionally, L-amino acids have been industrially produced by fermentation methods utilizing strains of microorganisms obtained from natural sources, or mutants of these strains which have been specifically modified to enhance L-amino acid productivity.

Many techniques for enhancing L-amino acid productivity have been disclosed, for example, by transformation of a microorganism with recombinant DNA (see, for example, U.S. Pat. No. 4,278,765). These techniques are based on increasing the activities of the enzymes involved in amino acid biosynthesis and/or desensitizing the enzymes subject to feedback inhibition by the L-amino acid (see, for example, Japanese Laid-open application No. 56-18596 (1981), WO 95/16042, or U.S. Pat. Nos. 5,661,012 and 6,040,160).

Alternatively, enhancing amino acid secretion may improve the productivity of a strain which can produce L-amino acids. *Corynebacterium*, which produce lysine and have increased expression of the L-lysine excretion gene (lysE gene), have been disclosed (WO 9723597A2). In addition, genes encoding efflux proteins suitable for secretion of L-cysteine, L-cystine, N-acetylserine or thiazolidine derivatives have also been disclosed (U.S. Pat. No. 5,972,663).

Several *Escherichia coli* genes have been disclosed which encode putative membrane proteins which function to increase L-amino acid production. The presence of additional copies of the rhtB gene cause a bacterium to become more resistant to L-homoserine, and therefore increase the production of L-homoserine, L-threonine, L-alanine, L-valine, and L-isoleucine by the bacterium (European patent application EP994190A2). The presence of additional copies of the rhtC gene cause a bacterium to become more resistant to L-homoserine and L-threonine, and therefore increase production of L-homoserine, L-threonine, and L-leucine (European patent application EP1013765A1). The presence of additional copies of the yahN, yeaS, yfiK, and yggA genes increase production of L-glutamic acid, L-lysine, L-threonine, L-alanine, L-histidine, L-proline, L-arginine, L-valine, and L-isoleucine (European patent application EP1016710A2).

The present inventors made a thrR mutant of *E.coli* K-12, also referred to as rhtA23, that displays resistance to high concentrations of threonine or homoserine in a minimal medium (Astaurova, O. B. et al., Appl. Biochem. Microbiol., 21, 611-616,1985). This mutation improved the production of L-threonine (SU Patent No. 974817), homoserine, and glutamate (Astaurova, O. B. et al., Appl. Biochem. Microbiol., 27, 556-561, 1991) by their respective *E. coli* producing strains.

Furthermore, the present inventors have reported that the rhtA gene is present at 18 min on the *E.coli* chromosome. This location is close to the glnHPQ operon that encodes components of the glutamine transport system. Also, the rhtA gene is identical to the ybiF ORF, which is located between the pexB and ompX genes. The DNA sequence expressing a protein encoded by this ORF has been designated the rhtA (rht: resistance to homoserine and threonine) gene.

The present inventors have also found that amplification of the rhtA gene confers resistance to homoserine and threonine. The rhtA23 mutation is an A-for-G substitution at position −1, with respect to the ATG start codon (ABSTRACTS of 17th International Congress of Biochemistry and Molecular Biology in conjugation with 1997 Annual Meeting of the American Society for Biochemistry and Molecular Biology, San Francisco, Calif. Aug. 24-29, 1997, abstract No. 457).

It is known that the nucleotide sequence of the spacer between the SD sequence and start codon, and especially the sequences immediately upstream of the start codon, profoundly affect mRNA translatability. A 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984). Therefore, these observations suggest that the rhtA23 mutation increases rhtA gene expression.

The rhtA gene encodes a protein of 295 amino acid residues and is a highly hydrophobic. There are 10 predicted transmembrane regions. A PSI-BLAST search of the nucleotide sequence of *E.coli* strain K-12 among the genus *Escherichia* (Science, 277, 1453-1474 (1997) revealed at least 10 proteins homologous to RhtA. Among these are proteins encoded by the ydeD and yedA genes. The ydeD gene is known to be involved in the efflux of cysteine pathway metabolites (Dasler et al., Mol. Microbiol., 36, 1101-1112, 2000; U.S. Pat. No. 5,972,663). The yedA gene is known as a putative transmembrane subunit, which encodes a protein for which the function is unknown (numbers 8037 to 8957 in the sequence of GenBank accession AE000287 U00096).

SUMMARY OF THE INVENTION

An object of present invention is to enhance the productivity of L-amino acid producing strains, and to provide a method for producing L-amino acids, for example, L-phenylalanine and L-threonine, using these strains.

These objects were achieved by identifying the yedA gene, which encodes a membrane protein which is a homologue to RhtA. This protein is not involved in any biosynthetic pathway of a target L-amino acid and confers resistance to several amino acids and amino acid analogues when the wild-type allele of the gene is amplified on a multicopy vector in a microorganism. The yedA gene can also increase amino acid production when additional copies of the gene are introduced into cells of a strain which produces the target amino acid. Thus, the present invention has been completed.

It is an object of the present invention to provide an L-amino acid producing *Escherichia* bacterium comprising an increased activity of a protein selected from the group consisting of:

(A) a protein comprising the amino acid sequence of SEQ ID NO:2;

(B) a protein comprising the amino acid sequence of SEQ ID NO:2, but which includes deletions, substitutions, insertions or additions of one or several amino acids, and which has an activity of inducing increased resistance to an L-amino acid, such as phenylalanine, threonine, homoserine, or cysteine, and/or an amino acid analog such as p-fluoro-phenylalanine, 5-fluoro-DL-tryptophane, S-(2-aminoethyl)cysteine, or 4-aza-DL-leucine.

It is a further object of the present invention to provide the bacterium as described above, wherein the activity of the protein is increased by transforming the bacterium with a DNA encoding said protein, or by altering an expression regulatory sequence of said DNA on the chromosome of the bacterium.

It is a further object of the present invention to provide the bacterium as described above, wherein the bacterium is transformed with a multicopy vector containing said DNA.

It is a further object of the present invention to provide a method for producing an L-amino acid comprising cultivating the bacterium as described above in a culture medium and collecting the L-amino acid from the culture medium or the bacterium.

It is a further object of the present invention to provide the method as described above, wherein the L-amino acid is L-phenylalanine.

It is a further object of the present invention to provide the method as described above, wherein expression of the genes involved in phenylalanine biosynthesis is increased.

It is a further object of the present invention to provide the method as described above, wherein the L-amino acid is L-threonine.

It is a further object of the present invention to provide the method as described above, wherein expression of the threonine operon is increased.

It is a further object of the present invention to provide a method for producing a lower alkyl ester of α-L-aspartyl-L-phenylalanine comprising cultivating the bacterium as described above in a culture medium, wherein said bacterium is able to produce L-phenylalanine, and synthesizing a lower alkyl ester of α-L-aspartyl-L-phenylalanine from aspartic acid or a derivative thereof and L-phenylalanine obtained from said bacterium.

It is a further object of the present invention to provide the method as described above, further comprising esterifying L-phenylalanine to generate a lower alkyl ester of L-phenylalanine, condensing the lower alkyl ester of L-phenylalanine with the aspartic acid derivative, wherein the derivative is N-acyl-L-aspartic anhydride, separating the lower alkyl ester of N-acyl-α-L-aspartyl-L-phenylalanine from the reaction mixture, and hydrogenating the lower alkyl ester of N-acyl-α-L-aspartyl-L-phenylalanine to generate the lower alkyl ester of α-L-aspartyl-L-phenylalanine.

In the present invention, an amino acid is in the L-configuration unless otherwise noted.

The method for producing an L-amino acid includes producing L-phenylalanine using an L-phenylalanine-producing bacterium wherein the activities of the proteins of the present invention, such as that of SEQ ID NO:2, are increased. Also, the method for producing L-amino acids also includes production of L-threonine using an L-threonine producing bacterium, wherein the activities of the proteins of the present invention, such as that of SEQ ID NO:2, are increased.

DESCRIPTION OF THE PREFERRED EMBODIMENTS

The present invention will be explained in detail below.

The bacterium of the present invention is an L-amino acid producing bacterium of the genus *Escherichia*, wherein the L-amino acid production by the bacterium is increased by increasing the activity of the proteins of the present invention in the bacterium.

In the present invention, "L-amino acid producing bacterium" means a bacterium which has an ability to produce and cause accumulation of the L-amino acid in a medium, when the bacterium is cultured in the medium. The L-amino acid producing ability may be inherent to the bacterium, or may be imparted or enhanced by breeding.

The bacterium of present invention is an L-amino acid producing bacterium of the genus *Escherichia* with increased activities of certain proteins, resulting in the increased production of target L-amino acids. More specifically, the bacterium of the present invention is an L-amino acid producing bacterium of the genus *Escherichia* that has increased activities of the proteins of the present invention. Even more specifically, the bacterium of the present invention overexpresses the yedA gene on the bacterial chromosome or in a plasmid in the bacterium, and as a result, the bacterium has increased ability to produce an L-amino acid, for example, L-phenylalanine and L-threonine.

The protein of the present invention includes the following:

(A) a protein of the amino acid sequence shown in SEQ ID NO:2;

(B) a variant of protein (A), which includes one or more deletions, substitutions, insertions, or additions in the amino acid sequence. This protein's or protein variant's activity results in enhanced resistance of the bacterium to L-amino acids, such as phenylalanine, threonine, homoserine, and cysteine, and/or amino acid analogs such as p-fluoro-phenylalanine, 5-fluoro-DL-tryptophane, S-(2-aminoethyl)cysteine, and 4-aza-DL-leucine.

The number of amino acids which can vary in the protein variant of SEQ ID NO: 2 depends on the position or type of amino acid residues in the three-dimensional structure of the protein. The number may be 1 to 30, preferably 1 to 15, and more preferably 1 to 5.

"Resistance of the bacterium to an L-amino acid and/or an amino acid analog" means that the bacterium retains the ability to grow on/in a minimal medium containing the particular L-amino acid or analog at a concentration which inhibits growth of an unmodified, wild-type, or parental strain of the bacterium. This phrase can also mean that the bacterium is able to grow faster in/on a medium containing the L-amino acid or amino acid analog as compared to an unmodified, wild-type, or parental strain of the bacterium. Examples of L-amino acid analogs include p-fluoro-phenylalanine, 5-fluoro-DL-tryptophan, S-(2-aminoethyl)cysteine, 4-aza-DL-leucine, and the like. The concentration of the L-amino acid or amino acid analog is generally 1000 to 10000 μg/ml, preferably 3000 to 5000 μg/ml for L-homoserine, preferably 5000 to 7000 μg/ml for serine and cysteine, generally 0.1 to 1.0 μg/ml, preferably 0.2 to 0.5 μg/ml for 5-fluoro-DL-tryptophan, generally 0.1 to 2.0 mg/ml, preferably 0.5 to 1.0 mg/ml for p-fluoro-phenylalanine; generally 0.1 to 2.0 mg/ml, preferably 0.5 to 1.0 mg/ml for 4-aza-DL-leucine and S-(2-aminoethyl)cysteine.

The bacterium of the present invention also includes one wherein the activities of the proteins of the present invention are increased by transforming said bacterium with DNA coding for the protein as defined above, or by altering an expression regulatory sequence of said DNA on the chromosome of the bacterium.

The DNA of the present invention may encode for a protein which has L-amino acid excretion activity. More specifically, the DNA is the yedA gene. The yedA gene can be obtained by, for example, PCR using primers based on the nucleotide sequence shown in SEQ ID No: 1.

The DNA of the present invention also includes a DNA encoding the protein variant as described above, which may include one or more deletions, substitutions, insertions or additions in the amino acid sequence of SEQ ID NO: 2 at one or more positions, as long as the activity of the protein is retained. Although the number of amino acids which may vary depends on the position or the type of the amino acid residue(s) in the three-dimensional structure of the protein, it may be 1 to 30, preferably 1 to 15, and more preferably 1 to 5. The DNA coding for the variant protein as described above may be obtained by, for example, modifying the nucleotide sequence coding for the protein of SEQ ID NO: 2 using site-directed mutagenesis. Such modified DNA can be obtained by conventional methods using treatment with reagents and under conditions which typically generate mutations. This includes treating the DNA with hydroxylamine, or treating the bacterium harboring the DNA with UV irradiation or a reagent such as N-methyl-N'-nitro-N-nitrosoguanidine or nitrous acid.

The DNA of the present invention includes DNA isolated from various strains and bacterial variants of *Escherichia*, but which differ in nucleotide sequence due to natural diversity. The DNA coding for such variants can be obtained by isolating DNA which hybridizes with the yedA gene or part of the gene under the stringent conditions, and which encodes a protein which increases L-amino acid production. The "stringent conditions" referred to herein are conditions under which so-called specific hybrid is formed, and non-specific hybrid is not formed. For example, stringent conditions include conditions under which DNAs having high homology, for instance DNAs having homology no less than 70% to each other, hybridize. Alternatively, stringent conditions are exemplified by typical conditions of washing during Southern hybridization, e.g., 60° C., 1×SSC, 0.1% SDS, preferably 0.1×SSC, 0.1% SDS. A partial sequence of the nucleotide sequence of SEQ ID NO: 1 can also be used. Such a probe may be prepared by PCR using oligonucleotides produced based on the nucleotide sequence of SEQ ID NO: 1 as primers, and a DNA fragment containing the nucleotide sequence of SEQ ID NO: 1 as a template. When a DNA fragment of about 300 bp is used as the probe, the washing conditions for the hybridization are, for example, 50° C., 2×SSC, and 0.1% SDS.

Transforming a bacterium with a DNA indicates the introduction of the DNA into the bacterial cell, for example, by conventional methods, to increase expression of the gene, which increases the activity of the encoded protein in the bacterial cell.

Increasing the gene copy number is a typical method for increasing gene expression. Introducing the gene into a vector capable of functioning in the chosen *Escherichia* bacterium increases the copy number of the gene. Multi-copy vectors are preferable, and include pBR322, pUC19, pBluescript KS+, pACYC177, pACYC184, pAYC32, pMW119, pET22b, and the like.

Increasing gene expression can be alternately achieved by introducing multiple copies of the gene into the bacterial chromosome by, for example, homologous recombination or the like.

When it is desired to increase the expression of two or more genes, the genes may be present on the same plasmid or each on a different plasmid. Also, one of the genes may be on the chromosome, and the other gene on a plasmid.

Alternatively, increasing gene expression can be achieved by locating the DNA of the present invention under the control of a potent promoter instead of the native promoter. The strength of a promoter is defined by the frequency of RNA synthesis initiation. Methods for evaluating the strength of a promoter and examples of potent promoters are described by Deuschle, U., Kammerer, W., Gentz, R., Bujard, H. (Promoters in *Escherichia coli*: a hierarchy of in vivo strength indicates alternate structures. EMBO J. 1986, 5,2987-2994). For example, the PL promoter of lambda phage is known as a potent constitutive promoter. Other known potent promoters are the lac promoter, trp promoter, trc promoter, and the like. Using a potent promoter can be combined with increasing the number of gene copies.

Methods for the preparation of chromosomal DNA, hybridization, PCR, preparation of plasmid DNA, digestion and ligation of DNA, transformation, selection of an oligonucleotide as a primer and the like may be typical methods well known to one skilled in the art. These methods are described in Sambrook, J., Fritsch, E. F., and Maniatis, T., "Molecular Cloning A Laboratory Manual, Third Edition", Cold Spring Harbor Laboratory Press (2001) and the like.

The bacterium of the present invention can be obtained by introducing the aforementioned DNAs into an *Escherichia* bacterium chosen for its ability to produce an L-amino acid. Alternatively, the bacterium of present invention can be obtained by imparting the ability to produce an L-amino acid to the chosen *Escherichia* bacterium which already harbors the DNAs.

The chosen *Escherichia* bacterium is not particularly limited so long as it has the ability to produce an L-amino acid or this ability can be imparted to it. Examples of *Escherichia* bacteria include *Escherichia coli*. Examples of amino acid-producing *Escherichia* bacteria are described below.

Phenylalanine Producing Bacteria

The *Escherichia* bacterial strains which produce phenylalanine include AJ12739 (tyrA::Tn10, tyrR) (VKPM B-8197), HW1089 (ATCC Accession No. 55371) which harbors the pheA34 gene (U.S. Pat. No. 5,354,672), mutant strain MWEC101-b (KR8903681), NRRL B-12141, NRRL B-12145, NRRL B-12146 and NRRL B-12147 strains (U.S. Pat. No. 4,407,952), and the like. The following strains may also be used as the parent strains which are then modified to increase the activity of the protein of the present invention: *E. coli* strain K-12 [W3110 (tyrA)/pPHAB (FERM BP-3566), *E. coli* strain K-12 [W3110 (tyrA)/pPHAD] (FERM BP-12659), *E. coli* K-12 [W3110 (tyrA)/pPHATerm] (FERM BP-12662), and *E. coli* strain K-12 [W3110 (tyrA)/pBR-aroG4,pACMAB] (AJ 12604 (FERM BP-3579)) (European patent EP488424B1).

Threonine Producing Bacteria

The *Escherichia* bacterial strains which produce threonine include MG442 (VKPM B-1628) (Gusyatiner, et al., Genetika (in Russian), 14, 947-956, 1978, U.S. Pat. No. 4,278, 765), VKPM B-3996 (U.S. Pat. No. 6,165,756), VKPM B-5318 (U.S. Pat. No. 6,132,999), BP-3756 and BP-4072 (U.S. Pat. No. 5,5,474,918), FERM BP-3519, FERM BP-3520 (U.S. Pat. No. 5,376,538), and the like.

The method of the present invention includes producing an L-amino acid by cultivating the bacterium of the present invention in a culture medium, to allow the L-amino acid to be produced and accumulated in the culture medium, and collecting the L-amino acid from the culture medium. Also, the method of the present invention includes producing L-phenylalanine by cultivating the bacterium of the present invention in a culture medium, to allow L-phenylalanine to be produced and accumulated in the culture medium, and collecting L-phenylalanine from the culture medium. Also, the method of the present invention includes producing L-threonine by cultivating the bacterium of the present invention in a culture medium, to allow L-threonine to be produced and accumulated in the culture medium, and collecting L-threonine from the culture medium.

The cultivation, collection, and purification of L-amino acids from the medium and the like may be performed in a manner similar to conventional fermentation methods wherein an amino acid is produced using a microorganism. The chosen culture medium may be either synthetic or natural, so long as it includes a carbon source, a nitrogen source, minerals, and if necessary, appropriate amounts of nutrients which the chosen bacteria might require for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganisms can be used. Minerals such potassium monophosphate, magnesium sulfate, sodium chloride, ferrous sulfate, manganese sulfate, calcium chloride, and the like can be used. Additional nutrients can be added to the medium if necessary. For instance, if the chosen microorganism requires tyrosine for growth (tyrosine auxotrophy), a sufficient amount of tyrosine can be added to the medium.

The cultivation is performed preferably under aerobic conditions such by shaking and/or stirring, with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to the accumulation of the target L-amino acid in the liquid medium.

After cultivation, solids such as cells can be removed from the liquid medium by centrifugation or membrane filtration, and then the target L-amino acid can be collected and purified by a conventional method such as ion-exchange, concentration and crystallization methods.

Phenylalanine produced by the method of the present invention may be used, for example, to produce lower alkyl esters of α-L-aspartyl-L-phenylalanine (also referred to as "aspartame"). That is, the method of the present invention includes production of lower alkyl esters of α-L-aspartyl-L-phenylalanine by using L-phenylalanine as a raw material. This is accomplished by synthesizing a lower alkyl ester of α-L-aspartyl-L-phenylalanine from L-phenylalanine, which is produced by the method of the present invention as described above, and aspartic acid or a derivative thereof. Lower alkyl esters include methyl ester, ethyl ester, and propyl ester, or the like.

In the method of the present invention, the process for synthesizing a lower alkyl esters of α-L-aspartyl-L-phenylalanine from L-phenylalanine and aspartic acid or its derivative is not particularly limited, and any conventional method can be used so long as L-phenylalanine or its derivative can be used as a starting material in the synthesis. More specifically, for example, a lower alkyl ester of α-L-aspartyl-L-phenylalanine may be produced by the process described in U.S. Pat. No. 3,786,039. L-phenylalanine is esterified to obtain the lower alkyl ester of L-phenylalanine. The L-phenylalanine alkyl ester is reacted with an L-aspartic acid derivative having a protected amino group and β-carboxyl group, and the β-carboxyl group is esterified. The derivative includes N-acyl-L-aspartic anhydride such as N-formyl-, N-carbobenzoxy-, or N-p-methoxycarbobenzoxy-L-aspartic anhydride. A mixture of N-acyl-α-L-aspartyl-L-phenylalanine and N-acyl-β-L-aspartyl-L-phenylalanine is obtained by a condensation reaction. If the condensation reaction is performed in the presence of an organic acid with a dissociation constant at 37° C. is $10^{-4}$ or less, the ratio of α to β forms to in the mixture is increased (Japanese Patent Laid-Open Publication No. 51-113841). Then, the N-acyl-α-L-aspartyl-L-phenylalanine is separated from the mixture, followed by hydrogenation, to obtain α-L-aspartyl-L-phenylalanine.

EXAMPLES

The present invention will be explained further with reference to the following non-limiting Examples.

Example 1

Cloning the yedA Gene from *E. coli*

The entire nucleotide sequence of *E. coli* strain K-12 has been determined (Science, 277, 1453-1474, 1997). A PSI-BLAST search revealed that at least 10 rhtA paralogues, including the yedA gene, are present in the *E. coli* K-12 genome. The yedA gene encodes a putative transmembrane subunit, the function of which is unknown.

Based on the reported nucleotide sequence, the primers depicted in SEQ ID Nos. 3 (primer 1) and 4 (primer 2) were synthesized. Primer 1 is complementary to the sequence from 179 to 153 nucleotides upstream of the start codon, and a BamHI restriction enzyme recognition site was introduced at the 5'-end thereof. Primer 2 is complementary to a sequence from 53 to 77 nucleotides downstream of the stop codon, and a SalI restriction enzyme recognition site was introduced at the 5'-end thereof.

The chromosomal DNA from the *E. coli* TG1 strain was prepared by typical methods. PCR was carried out on a Perkin Elmer GeneAmp PCR System 2400 as follows: 40 sec. at 95° C., 40 sec. at 47° C., 40 sec. at 72° C.; 30 cycles with Taq polymerase (Fermentas). A PCR fragment containing the yedA gene with its own promoter was obtained and treated with the BamHI and SalI restrictases, and inserted into multicopy vectors pUC19 or pAYCTER3, which had been previously treated with the same enzymes. Thus, the plasmids pYEDA1 and pYEDA2, respectively, were obtained. The pAYCTER3 vector is a derivative of pAYC32, which is a moderate copy number and very stable vector constructed from plasmid RSF1010 (Christoserdov A. Y., Tsygankov Y. D, Broad-host range vectors derived from a RSF1010 Tnl plasmid, Plasmid, 1986, v. 16, pp. 161-167). The pAYCTER3 vector was obtained by introducing the polylinker from pUC19 and the strong terminator rrnB into pAYC32 instead of its native promoter as follows. First, the polylinker from pUC19 was obtained by PCR using the primers depicted in SEQ ID Nos. 5 and 6. The PCR product was treated with EcoRI and BglII restrictases. The terminator rrnB also was obtained by PCR using the primers depicted in SEQ ID Nos. 7 and 8. The PCR product was treated with BglII and BclI restrictases. Then, these two DNA fragments were ligated into pAYC32 which had been previously treated with EcoRI and BclI restrictases. Thus, the pAYCTER3 plasmid was obtained.

Example 2

The Effect of Amplifying the yedA Gene on the Resistance of *E. coli* Strain TG1 to Amino Acids and Amino Acid Analogs The pYEDA1 and pYEDA2 plasmids and the pUC19 and pAYCTER3 vectors were introduced into *E. coli* strain TG1. Thus the strains TG1 (pYEDA1), TG1 (pYEDA2), TG1 (pUC19) and TG1 (pAYCTER3) were obtained.

Then the ability of each strain to grow in the presence of amino acids and amino acid analogues was determined on M9 glucose minimal agar plates containing graded concentrations of inhibitor. The plates were spotted with 106 to 107 cells from an overnight culture grown in a minimal medium (supplemented with 100 μg/ml of ampicillin for plasmid strains). The growth was determined after incubation for 44 h at 37° C. The results are presented in Table 1.

TABLE 1

| Substrate | Concentration mg/ml | Growth after 44 h | | |
|---|---|---|---|---|
| | | TG1 (pUC19)* | TG1 (pYEDA1) | TG1 (pYEDA2) |
| — | — | + | + | + |
| L-Phenylalanine | 20.0 | − | + | − |
| L-homoserine | 3.0 | − | + | n.d. |
| L-threonine | 50.0 | − | + | n.d. |
| L-cysteine | 7.5 | − | + | n.d. |
| L-histidine | 20.0 | − | + | n.d. |
| p-fluoro-DL-phenylalanine | 1.0 | − | + | + |
| p-fluoro-DL-phenylalanine | 2.0 | − | + | − |
| 5-fluoro-DL-tryptophan | 0.0005 | − | + | n.d. |
| S(2-aminoethyl)-L-cysteine | 0.4 | − | + | + |
| 4-aza-DL-leucine | 1.0 | − | + | n.d. |

*The same results were obtained for the TG1 strain harboring pAYCTER3 vector.
+: good growth;
−: no growth;
n.d.—not determined.

Example 3

Effect of Amplification of the yedA Gene on Phenylalanine Production

The phenylalanine-producing *E.coli* strain AJ12739 was used as a parental strain for transformation with plasmids harboring the yedA gene. This strain AJ12739 was deposited in the Russian National Collection of Industrial Microorganisms (VKPM) (Russia, 113545 Moscow, 1st Dorozhnyproezd, 1) on Nov. 6, 2001 under accession number VKPM B-8197. The deposit was converted to an international deposit according to the Budapest Treaty on Aug. 23, 2002.

AJ12739 was transformed with the pYEDA2 plasmid or with the pAYCTER3 vector to obtain the AJ12739/pYEDA2 and AJ12739/pAYCTER3 strains. These strains were each cultivated at 37° C. for 18 hours in a nutrient broth with 100 mg/l ampicillin, and 0.3 ml of the obtained culture were inoculated into 3 ml of a fermentation medium containing 100 mg/l ampicillin, in a 20×200 mm test tube, and cultivated at 37° C. for 48 hours in a rotary shaker. After the cultivation, the amount of phenylalanine which had accumulated in the medium was determined by TLC. 10×15 cm TLC plates coated with 0.11 mm layers of Sorbfil silica gel without fluorescent indicator (Stock Company Sorbpolymer, Krasnodar, Russia) were used. Sorbfil plates were developed with a mobile phase: propan-2-ol:ethylacetate:25% aqueous ammonia:water=40:40:7:16 (v/v). A solution (2%) of ninhydrin in acetone was used as a visualizing reagent.

The results are presented in Table 2.

The composition of the fermentation medium (g/l):

| | |
|---|---|
| Glucose | 40.0 |
| $(NH_4)_2SO_4$ | 16.0 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine-HCl | 0.0002 |
| Yeast extract | 2.0 |
| Tyrosine | 0.1 |
| $CaCO_3$ | 30.0 |

Glucose and magnesium sulfate are sterilized separately. $CaCO_3$ dry-heat are sterilized at 180° C. for 2 h. pH is adjusted to 7.0. Antibiotic is introduced into the medium after sterilization.

TABLE 2

| *E. coli* strain | OD600 | Phenylalanine, g/l |
|---|---|---|
| AJ12739(pAYCTER3) | 7.0 | 1.5 |
| AJ12739(pAYCTER-YEDA2) | 7.5 | 1.8 |

It can be seen from the Table 2 that the yedA gene amplification improved phenylalanine productivity by the AJ12739 strain.

Example 4

Effect of Amplification of the yedA Gene on Threonine Production

The known threonine-producing *E. coli* strain VNII Genetika MG442 (Gusyatiner, et al., 1978, Genetika (in Russian), 14, p. 947-956) (deposited in the Russian National Collection of Industrial Microorganisms (VKPM) according to the Budapest Treaty under accession number VKPM B-1628) was transformed with the pYEDA1 plasmid or with the pUC19 vector, resulting in the strains MG442/pYEDA1 and MG442/pUC19.

These strains were each cultivated at 37° C. for 18 hours in a nutrient broth with 100 mg/l ampicillin, and 0.3 ml of the culture was inoculated into 3 ml of a fermentation medium containing 100 mg/l ampicillin, in a 20×200 mm test tube, and cultivated at 37° C. for 48 hours in a rotary shaker. After the cultivation, the amount of threonine which had accumulated in the medium was determined by TLC. Sorbfil plates were developed with a mobile phase: propan-2-ol:acetone:water: 25% aqueous ammonia=25:25:7:6 (v/v). A solution (2%) of ninhydrin in acetone was used as a visualizing reagent. The results are presented in Table 3.

The composition of the fermentation medium (g/l):

| | |
|---|---|
| Glucose | 50.0 |
| $(NH_4)_2SO_4$ | 10.0 |
| $K_2HPO_4$ | 1.0 |
| $MgSO_4 \cdot 7H_2O$ | 0.4 |

-continued

| | |
|---|---|
| FeSO$_4$·7H$_2$O | 0.02 |
| MnSO4·5H$_2$O | 0.02 |
| Thiamine-HCl | 0.0002 |
| Yeast extract | 1.0 |
| CaCO$_3$ | 20.0 |

Glucose and magnesium sulfate are sterilized separately. CaCO$_3$ dry-heat are sterilized at 180° C. for 2 h. pH is adjusted to 7.0. Antibiotic is introduced into the medium after sterilization.

TABLE 3

| E. coli strain | Threonine, g/l | Yield, (%) |
|---|---|---|
| MG442(pUC19) | 2.9 | 5.8 |
| MG442(pYEDA1) | 4.0 | 8.0 |

It can be seen from the Table 2 that the yedA gene amplification improved threonine productivity of the MG442 strain.

What is claimed is:

1. A method for producing a lower alkyl ester of α-L-aspartyl-L-phenylalanine selected from the group consisting of methyl ester, ethyl ester, propyl ester, and combinations thereof, comprising A) producing L-phenylalanine by cultivating an *Escherichia coli* bacterium in a medium, wherein said bacterium has the ability to produce L-phenylalanine, B) esterifying the L-phenylalanine to generate a lower alkyl ester of L-phenylalanine selected from the group consisting of methyl ester, ethyl ester, propyl ester, and combinations thereof, C) condensing said lower alkyl ester of L-phenylalanine with N-acyl-L-aspartic anhydride to obtain the lower alkyl ester of N-acyl-α-L-aspartyl-L-phenylalanine, D) separating the lower alkyl ester of N-acyl-α-L-aspartyl-L-phenylalanine from the reaction mixture obtained in step C), and E) hydrogenating the lower alkyl ester of N-acyl-α-L-aspartyl-L-phenylalanine to generate the lower alkyl ester of α-L-aspartyl-L-phenylalanine, wherein said bacterium has been modified so that the L-phenylalanine production by said bacterium is increased as compared to the corresponding unmodified bacterium by increasing the expression of a DNA selected from the group consisting of:

a) a DNA comprising the nucleotide sequence of SEQ ID NO: 1, and b) a DNA encoding a protein comprising the amino acid sequence of SEQ ID NO: 2, except that the sequence may include deletions, substitutions, insertions, or additions of 1 to 5 amino acids, and wherein said protein has an activity of imparting upon a bacterium resistance to an L-amino acid selected from the group consisting of L-phenylalanine, L-threonine, L-homoserine, L-cysteine and L-histidine, and/or imparting upon a bacterium resistance to an amino acid analog selected from the group consisting of p-fluoro-phenylalanine, 5-fluoro-DL-tryptophan, S-(2-aminoethyl) cysteine, and 4-aza-DL-leucine, and wherein said expression is increased by a method selected from the group consisting of increasing the copy number of said DNA in said bacterium, locating said DNA under the control of a potent promoter instead of the native promoter on the chromosome of the bacterium, and a combination thereof.

2. The method of claim 1, wherein said *Escherichia coli* bacterium has been modified so that the L-phenylalanine production by said bacterium is increased as compared to the corresponding unmodified bacterium by increasing the expression of a DNA that encodes a protein comprising the amino acid sequence of SEQ ID NO:2, wherein said expression is increased by a method selected from the group consisting of increasing the copy number of said DNA in said bacterium as compared to the corresponding unmodified bacterium, locating said DNA under the control of a potent promoter instead of the native promoter on the chromosome of the bacterium, and a combination thereof.

3. The method of claim 1, wherein said DNA is present on a multicopy vector.

4. The method of claim 2, wherein said DNA is present on a multicopy vector.

5. The method according to claim 1, wherein the bacterium has increased expression of the genes for phenylalanine biosynthesis as compared to the corresponding unmodified bacterium.

* * * * *

SEQUENCE LISTING

<160> NUMBER OF SEQ ID NOS: 8

<210> SEQ ID NO 1
<211> LENGTH: 921
<212> TYPE: DNA
<213> ORGANISM: Escherichia coli

<400> SEQUENCE: 1

```
atgcgtttcc gccagttgtt accgcttttt ggcgcgctgt ttgcgttgta tatcatttgg      60
ggctcaacct attttgtcat tcggattggc gtggaaagct ggcctccgtt aatgatggcg     120
ggcgttcgat tcctggcagc cggtattttta ttgctggcat ttttgctact gcgcggacac     180
aaactccccc cgctacgtcc gctgctcaat gccgcgctga ttggcctgtt attgctggct     240
gtcggtaatg gcatggtgac ggttgccgaa catcaaaatg ttccttccgg catcgccgcc     300
gtagtggttg caaccgtgcc cctctttacc ctgtgcttca gccgcctgtt tggcattaaa     360
acgcgcaaac tggaatgggt gggtattgcc attgggcttg ccggaatcat catgctcaat     420
agcggtggaa atttaagcgg caatccgtgg ggcgcgattc tgattttaat cggctcgatt     480
agctgggcgt ttggctcagt ttatggctcg cgcattacct tacctgtagg gatgatggcg     540
ggtgcgattg agatgctggc ggcaggcgtg gtgttaatga tcgcgtcgat gattgcgggt     600
gaaaaactga cggcgctccc ttcccttttca ggcttccttg cggtcggcta tctggcgctg     660
tttggttcga ttatcgccat caacgcttat atgtatttaa tccgtaatgt cagtccggct     720
ctcgccacca gctacgctta cgttaacccg gtggtcgcgg tcttgctggg tacgggactg     780
ggtggagaaa cactgtcgaa gattgaatgg ctggcgctcg gcgtaattgt cttcgcggtg     840
gtactggtca cgttgggaaa atatctcttc ccggcaaaac ccgtagttgc gccagttatt     900
caggacgcat caagcgagta a                                               921
```

<210> SEQ ID NO 2
<211> LENGTH: 306
<212> TYPE: PRT
<213> ORGANISM: Escherichia coli

<400> SEQUENCE: 2

```
Met Arg Phe Arg Gln Leu Leu Pro Leu Phe Gly Ala Leu Phe Ala Leu
 1               5                  10                  15

Tyr Ile Ile Trp Gly Ser Thr Tyr Phe Val Ile Arg Ile Gly Val Glu
            20                  25                  30

Ser Trp Pro Pro Leu Met Met Ala Gly Val Arg Phe Leu Ala Ala Gly
        35                  40                  45

Ile Leu Leu Leu Ala Phe Leu Leu Arg Gly His Lys Leu Pro Pro
    50                  55                  60
```

Leu Arg Pro Leu Leu Asn Ala Ala Leu Ile Gly Leu Leu Leu Ala
65                  70                  75                  80

Val Gly Asn Gly Met Val Thr Val Ala Glu His Gln Asn Val Pro Ser
                85                  90                  95

Gly Ile Ala Ala Val Val Ala Thr Val Pro Leu Phe Thr Leu Cys
            100                 105                 110

Phe Ser Arg Leu Phe Gly Ile Lys Thr Arg Lys Leu Glu Trp Val Gly
            115                 120                 125

Ile Ala Ile Gly Leu Ala Gly Ile Ile Met Leu Asn Ser Gly Asn
130                 135                 140

Leu Ser Gly Asn Pro Trp Gly Ala Ile Leu Ile Leu Ile Gly Ser Ile
145                 150                 155                 160

Ser Trp Ala Phe Gly Ser Val Tyr Gly Ser Arg Ile Thr Leu Pro Val
                165                 170                 175

Gly Met Met Ala Gly Ala Ile Glu Met Leu Ala Ala Gly Val Val Leu
                180                 185                 190

Met Ile Ala Ser Met Ile Ala Gly Glu Lys Leu Thr Ala Leu Pro Ser
                195                 200                 205

Leu Ser Gly Phe Leu Ala Val Gly Tyr Leu Ala Leu Phe Gly Ser Ile
210                 215                 220

Ile Ala Ile Asn Ala Tyr Met Tyr Leu Ile Arg Asn Val Ser Pro Ala
225                 230                 235                 240

Leu Ala Thr Ser Tyr Ala Tyr Val Asn Pro Val Val Ala Val Leu Leu
                245                 250                 255

Gly Thr Gly Leu Gly Gly Glu Thr Leu Ser Lys Ile Glu Trp Leu Ala
                260                 265                 270

Leu Gly Val Ile Val Phe Ala Val Leu Val Thr Leu Gly Lys Tyr
                275                 280                 285

Leu Phe Pro Ala Lys Pro Val Val Ala Pro Val Ile Gln Asp Ala Ser
            290                 295                 300

Ser Glu
305

<210> SEQ ID NO 3
<211> LENGTH: 25
<212> TYPE: DNA
<213> ORGANISM: Artificial Sequence
<220> FEATURE:
<223> OTHER INFORMATION: synthetic DNA

<400> SEQUENCE: 3
aagggatccc tctcattttt attgt                                    25

<210> SEQ ID NO 4
<211> LENGTH: 23
<212> TYPE: DNA
<213> ORGANISM: Artificial Sequence
<220> FEATURE:
<223> OTHER INFORMATION: synthetic DNA

<400> SEQUENCE: 4
aagcgtcgac cgagcgtctg gaa                                      23

<210> SEQ ID NO 5
<211> LENGTH: 29
<212> TYPE: DNA
<213> ORGANISM: Artificial Sequence
<220> FEATURE:

-continued

```
<223> OTHER INFORMATION: synthetic DNA

<400> SEQUENCE: 5
gaccatagat ctgaattcga gctcggtac                                              29

<210> SEQ ID NO 6
<211> LENGTH: 29
<212> TYPE: DNA
<213> ORGANISM: Artificial Sequence
<220> FEATURE:
<223> OTHER INFORMATION: synthetic DNA

<400> SEQUENCE: 6
acggccagat ctaagcttgc atgcctgca                                              29

<210> SEQ ID NO 7
<211> LENGTH: 34
<212> TYPE: DNA
<213> ORGANISM: Artificial Sequence
<220> FEATURE:
<223> OTHER INFORMATION: synthetic DNA

<400> SEQUENCE: 7
aacagtgatc atttgcctgg cggcagtagc gcgg                                        34

<210> SEQ ID NO 8
<211> LENGTH: 41
<212> TYPE: DNA
<213> ORGANISM: Artificial Sequence
<220> FEATURE:
<223> OTHER INFORMATION: synthetic DNA

<400> SEQUENCE: 8
ataaaaagct tagatctcaa aaagagtttg tagaaacgca a                                41
```